United States Patent
Coleman et al.

(10) Patent No.: US 6,881,202 B2
(45) Date of Patent: Apr. 19, 2005

(54) NEEDLE ASSEMBLY

(75) Inventors: John D. Coleman, Philadelphia, PA (US); Peter Bressler, Philadelphia, PA (US); Jordan DeLiso, Hillsdale, NJ (US); Bradley M. Wilkinson, North Haledon, NJ (US); Mathieu Turpault, Berwyn, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 15 days.

(21) Appl. No.: 10/414,543

(22) Filed: Apr. 15, 2003

(65) Prior Publication Data

US 2003/0225375 A1 Dec. 4, 2003

Related U.S. Application Data

(60) Provisional application No. 60/383,521, filed on May 28, 2002.

(51) Int. Cl.⁷ ................................................ A61M 5/32
(52) U.S. Cl. .................................. 604/177; 604/165.03
(58) Field of Search ............................ 604/110, 165.01, 604/165.02, 165.03, 165.04, 177, 163, 263, 164.04, 164.13, 174

(56) References Cited

U.S. PATENT DOCUMENTS 5,382,240 A   1/1995   Lam
5,498,241 A * 3/1996   Fabozzi ...................... 604/177
5,879,334 A   3/1999   Brimhall
6,210,371 B1  4/2001   Shaw

FOREIGN PATENT DOCUMENTS

EP   0 499 077      8/1992
WO   WO 98/42393    10/1998

* cited by examiner

*Primary Examiner*—Kevin C. Sirmons
(74) *Attorney, Agent, or Firm*—Scott J. Rittman, Esq.; Mark Lindsey

(57) ABSTRACT

A shieldable winged needle assembly includes a hub and a cannula projecting distally beyond the hub. A spring is telescoped over the cannula and engages with or into distal portions of the hub. A hub guide projects radially out from the hub. A first wing includes a center sleeve rotationally mounted on the hub and axially movable along the hub when a slot formed in the center sleeve aligns with the hub guide. A second wing has proximal and distal sleeves mounted at opposite ends of the center sleeve. The proximal and distal sleeves each are rotationally mounted relative to the hub and each include slots that enable sliding movement of the hub guide when the slots of the second wing align with the slot of the first wing. The spring propels the cannula and hub into a shielding position when the slots of the wings are rotated into alignment with one another.

19 Claims, 13 Drawing Sheets

NEEDLE ASSEMBLY

RELATED APPLICATIONS

This application claims priority on U.S. Provisional Patent Appl. No. 60/383,521 filed May 28, 2002.

BACKGROUND OF THE INVENTION

1. Field of the Invention

The invention relates to needle protection devices, and particularly a safety device for use with an intravenous infusion needle.

2. Description of the Related Art

A device commonly referred to as a "butterfly" or winged intravenous infusion assembly often is used for IV infusions and/or for withdrawing venous blood. This device also may be known as a hemodialysis needle. The device typically includes a needle hub with opposite proximal and distal ends and a passage extending between the ends. The device also includes a needle cannula with a proximal end, a sharply pointed distal end and a lumen extending between the ends. The proximal end of the needle cannula is securely mounted in the hub of the device so that the lumen through the needle cannula communicates with the passage through the hub. The device may further include a length of flexible plastic tubing with opposite proximal and distal ends. The proximal end of the tubing typically is mounted to a fitting, such as a luer fitting. The distal end of the tubing is mounted to the proximal end of the hub. Thus, communication is provided between the lumen of the needle cannula and the fitting at the proximal end of the flexible tubing.

The device is employed by placing the pointed distal end of the needle cannula in, communication with a blood vessel and placing the fitting at the proximal end of the flexible tubing in communication with a container that will be used to infuse a drug into the patient or to collect a specimen of blood from the patient. The needle may remain in communication with the patient for an extended time. Hence, it is common to tape the device to the skin of the patient to prevent a painful shifting of the needle relative to the patient. The needle cannula and the hub are very small. Accordingly, wings are provided to manipulate the needle cannula during insertion into the targeted blood vessel. The wings can be folded into face-to-face engagement with one another and gripped between a thumb and forefinger. Thus, the folded wings function as a handle to facilitate proper alignment of the needle cannula during insertion into the blood vessel. The wings then can be rotated into a substantially co-planar disposition and can be taped into face-to-face engagement with the skin of the patient.

Accidental sticks with a used needle cannula can transmit blood-borne diseases. Thus, some states mandate protection devices to reduce the risk of accidental sticks with a used needle cannula. A very effective needle protection device for IV infusion needles is marketed by Becton Dickinson and Company under the trademark SAFETY-LOCK™. Another safety needle protection system for IV infusion needles is marketed by Sherwood Medical Company and sold under the trademark ANGEL WING™. These systems require a user to grip the wings with one hand and the shield with the other hand. The hands then are moved relative to one another to retract the needle relative to the shield or to move the shield over the needle. Shielding may not be completed properly if the user forgets to perform the two-handed shielding operation or if the exigencies of the medical situation prevent the user from performing the two-handed shielding operation. Additionally, a potential exists that the user will not perform the manual shielding operation properly or completely. Hence, the used needle could be re-exposed prior to being discarded.

In view of the above, it is an object of the subject invention to provide a needle assembly that permits one-handed shielding of an IV infusion needle.

It is another object of the subject invention to provide an IV infusion needle assembly that permits shielding to be effected automatically as part of the process of removing the used needle cannula from the patient.

SUMMARY OF THE INVENTION

The subject invention relates to a medical device, such as an IV infusion set or blood collection set. For simplicity, the device will be referred to herein as an IV infusion set. The IV infusion set includes a needle assembly with a needle hub that has a proximal end, a distal end and a passage extending between the ends. External portions of the hub are provided with a guide. The guide may be a projection that extends in a direction transverse to the passage through the hub, and preferably is formed near the distal end of the hub. The hub may further include a generally cylindrical spring recess extending into the distal end of the hub at a location spaced outwardly from the passage and spaced inwardly from the outer surface of the hub. The needle assembly further includes a needle cannula having a proximal end, a sharply pointed distal end and a lumen extending between the ends. The proximal end of the needle cannula is mounted in the passage of the hub, and the pointed distal end of the needle cannula projects distally beyond the hub.

The IV infusion set may further include a length of flexible plastic tubing that has a proximal end, a distal end, and a passage extending between the ends. The proximal end of the flexible plastic tubing may be mounted securely to a fitting, such as a female luer fitting. The distal end of the flexible plastic tubing may be mounted to the proximal end of the hub. Thus, the lumen through the needle cannula communicates with the fitting at the proximal end of the flexible plastic tubing.

The needle assembly further includes first and second wings. The first wing includes a generally planar panel and a center sleeve that is mounted over the hub for both rotational movement and axial sliding movement. The center sleeve has opposite proximal and distal ends and a longitudinal slot extending continuously between the ends. The slot may extend completely through the wall of the sleeve to define a split tube. However, the slot also can be formed only in the inner circumferential surface of the sleeve, and hence may be more in the nature of a groove. The slot defines a circumferential dimension or width that is equal to or slightly greater than the circumferential dimension of the projection on the hub. Thus, the projection on the hub can slide longitudinally through the slot on the center sleeve when the slot of the center sleeve is aligned rotationally with the projection on the hub. However, the center sleeve and the hub are fixed longitudinally relative to one another when the slot in the center sleeve is rotationally offset from the projection on the hub.

The second wing includes proximal and distal components that are assembled to one another and securely connected after assembly. The proximal component of the second wing includes a generally planar proximal panel and a proximal sleeve that is telescoped over proximal portions of the hub and over distal portions of the flexible tubing. The proximal sleeve is dimensioned and configured for rotational movement about the hub and for longitudinal movement relative to the hub. The proximal sleeve may further include a longitudinally extending slot with a circumferential dimension or width that exceeds circumferential dimension or width of the projection on the hub. The slot in the proximal sleeve may extend completely through the wall of the sleeve in a radial direction or may be a groove in the inner circumferential surface of the sleeve. However, the slot in the proximal sleeve preferably extends only from the distal end of the proximal mounting sleeve to a location between the proximal and distal ends thereof. The length of the slot in the proximal sleeve is equal to or greater than the axial length of the projection on the hub.

The distal component of the second wing includes a distal panel and a distal sleeve. The distal panel is dimensioned and configured to mate with the proximal panel. The distal sleeve is dimensioned to mount over the distal end of the hub and over portions of the needle cannula. The distal sleeve further includes a longitudinally extending slot that is wider than the projection of the hub. The slot in the distal sleeve may extend completely through the wall of the sleeve or may be a groove in the inner circumferential surface of the sleeve. The slot in the distal sleeve extends from the proximal end of the distal sleeve to a location between the proximal and distal ends, and has an axial length that exceeds the axial length of the projection on the hub.

The second wing is assembled such that the proximal and distal sleeves are disposed respectively at the proximal and distal ends of the center sleeve of the first wing. Additionally, the slots in the proximal and distal sleeves align with one another and can both be placed in alignment with the slot of the center sleeve by appropriate rotation of the first and/or second wings relative to one another.

The needle assembly may further include a spring disposed between the hub and at least one of the sleeves. The spring is operative to bias the hub proximally relative to the wings.

The wings of the needle assembly initially may be in a substantially coplanar disposition with the hub and needle cannula advanced into an extreme distal position relative to the wings. In this position, the projection of the hub is disposed in the slot in the distal sleeve and the spring is in a biased condition. The slot in the center sleeve is offset rotationally from the slot in the distal sleeve. Hence, the projection is prevented from moving through the slot in the center sleeve, and the needle cannula is retained in a position projecting distally beyond the wings.

The needle assembly of the IV infusion set may be used by rotating the wings upwardly and toward one another so that the wings may function as a convenient handle to be gripped between a thumb and forefinger. This rotational movement of the wings toward one another may rotationally displace the slot in the center sleeve further from the slot in the distal sleeve. Hence, the projection of the hub remains trapped distally of the center sleeve and the needle cannula remains projected distally beyond the wings. The needle cannula then is guided into a targeted blood vessel of a patient. The wings then may be rotated back into their coplanar disposition and may be taped in substantially face-to-face engagement with the skin of the patient.

Upon completion of the medical procedure, the needle cannula is withdrawn from the patient and the wings are rotated down and toward one another. This rotational movement of the first and second wings down and toward one another moves the slot of the center sleeve into alignment with the projection on the hub. As a result, the spring biases the hub proximally and causes the projection of the hub to move proximally through the slot of the center sleeve and into the slot of the proximal sleeve. This proximal movement of the hub by the spring causes the needle cannula to be retracted safely within the sleeves of the first and second wings. The spring maintains its biasing force to keep the needle cannula in the safely shielded position. Additionally, further downward rotation of the wings may move the slot of the center sleeve beyond the projection of the hub. Thus, the center sleeve retains the projection in the slot of the proximal sleeve and holds the needle cannula in the shielded position.

DETAILED DESCRIPTION

Figure 1:
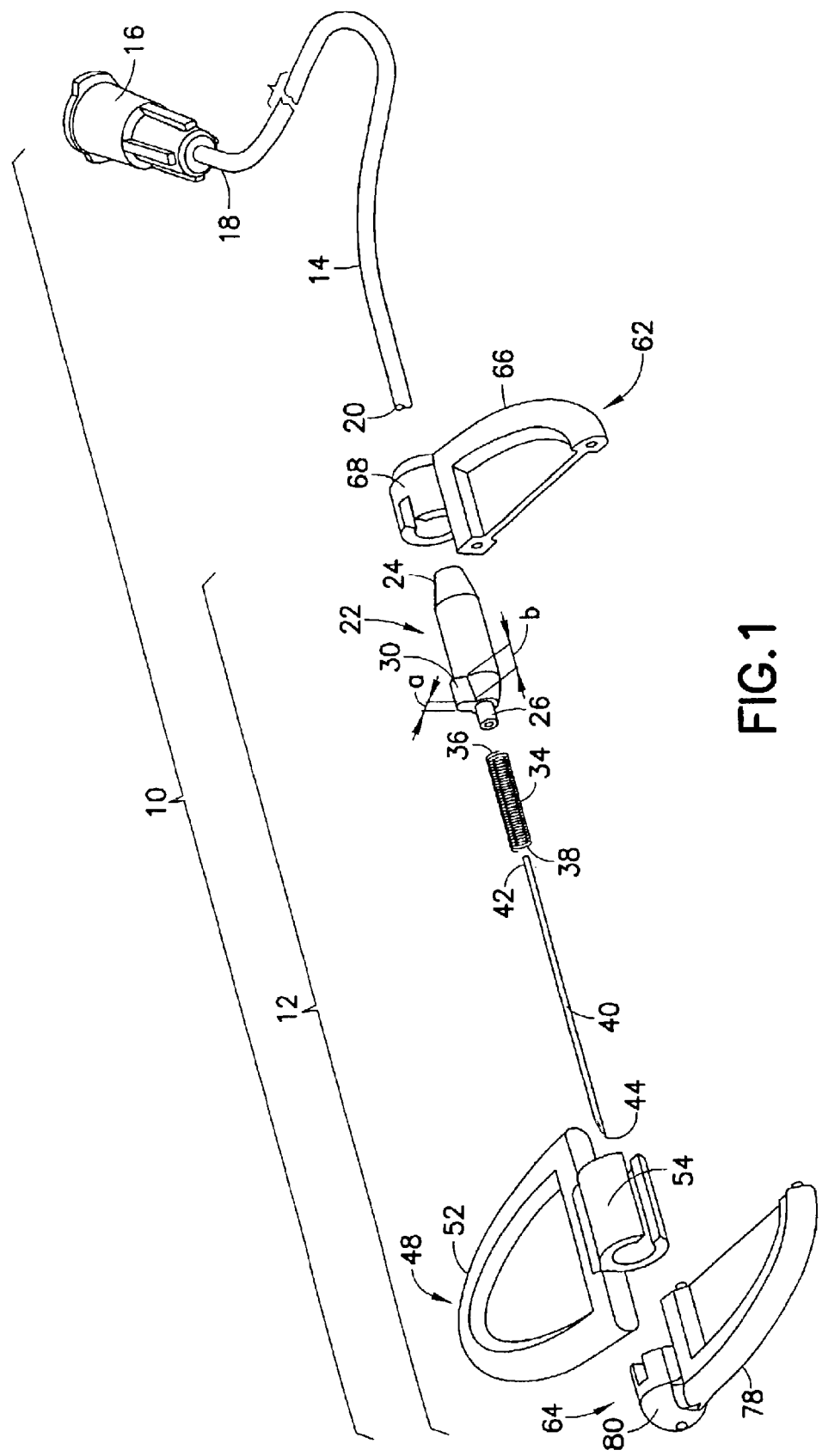
FIG. 1 is an exploded perspective view of an IV infusion set in accordance with the subject invention.
Figure 2:
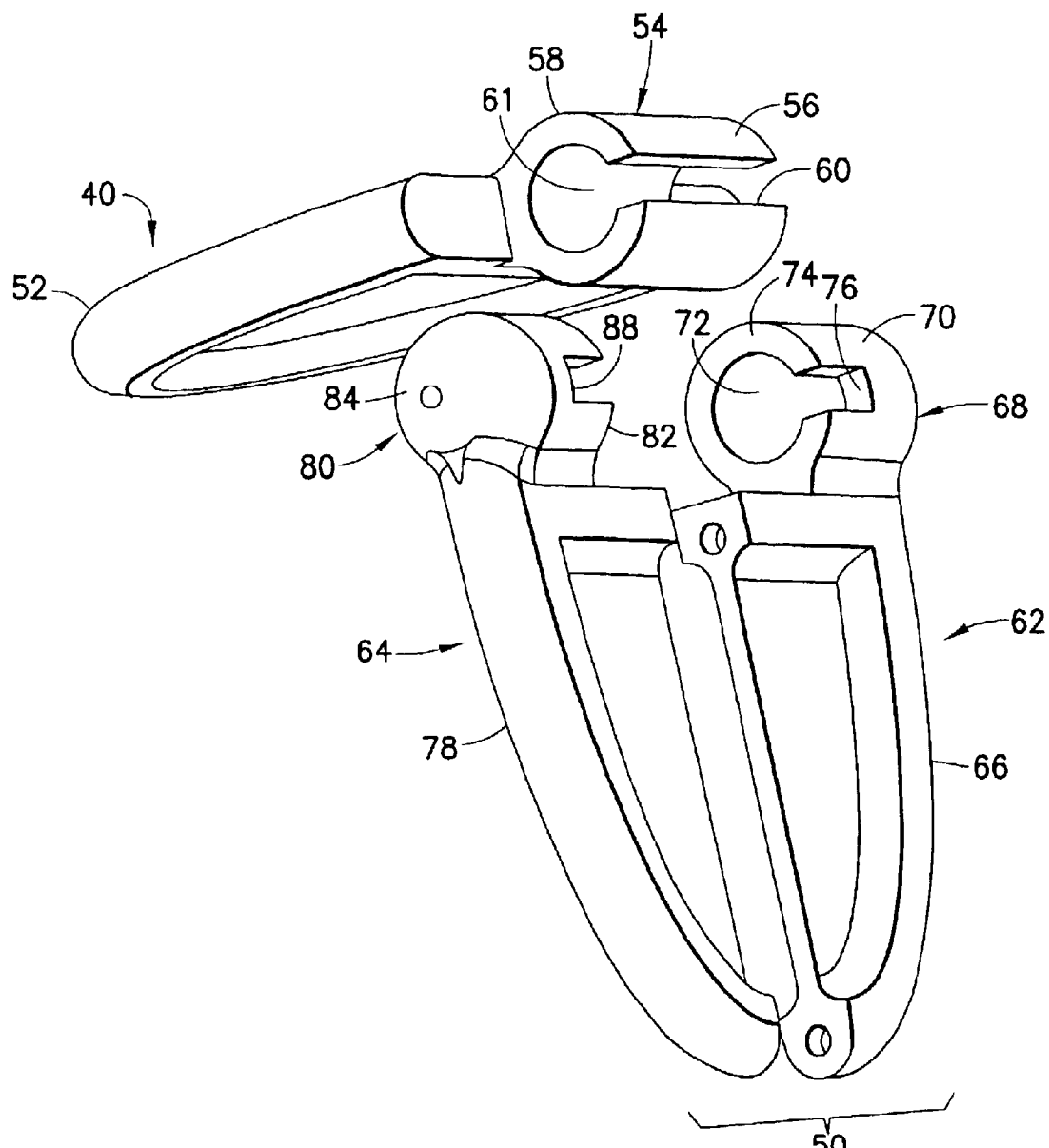
FIG. 2 is an exploded perspective view of the wings as seen from the front.
Figure 3:
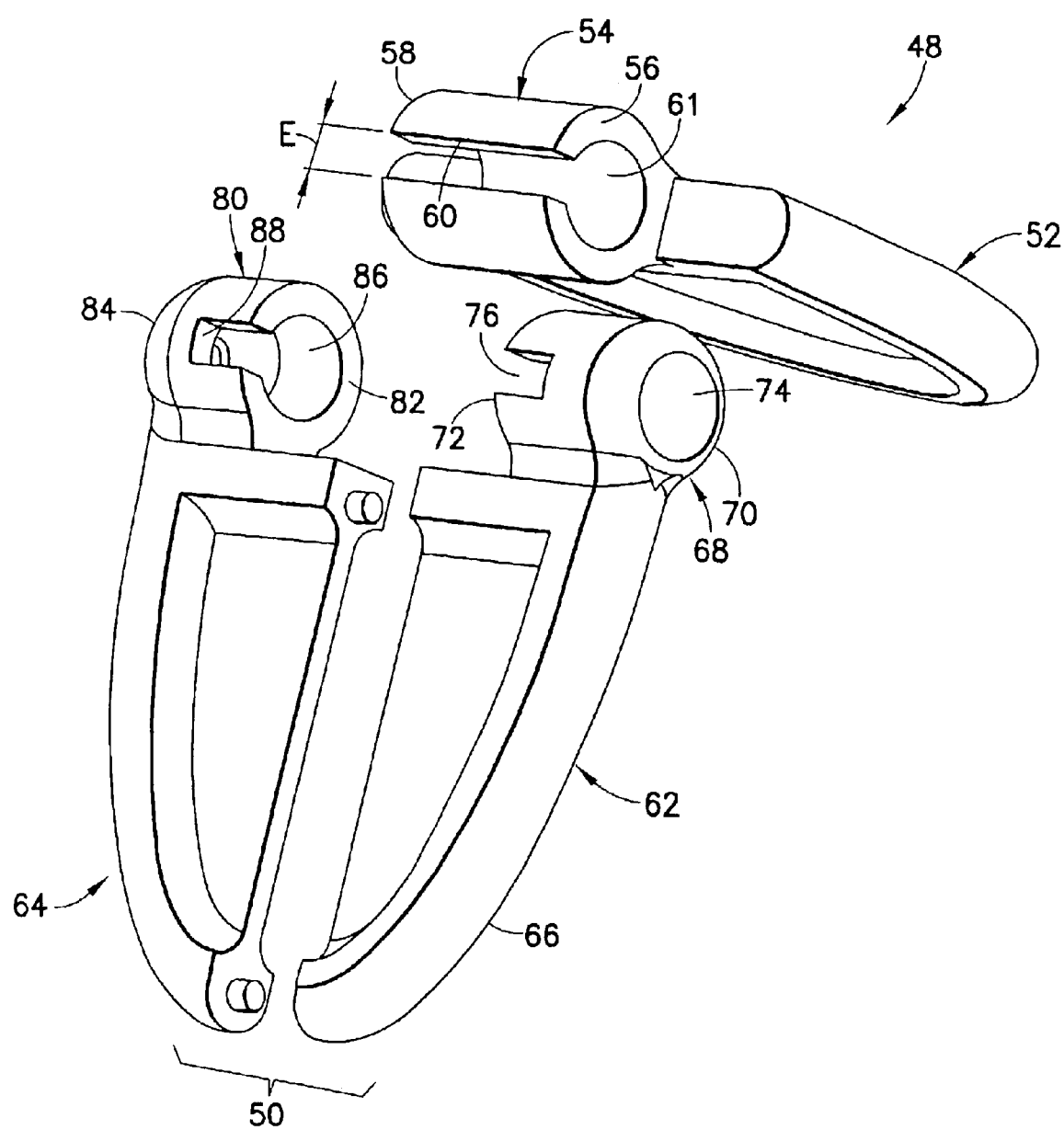
FIG. 3 is an exploded perspective view of the wings as seen from the rear.
Figure 10:
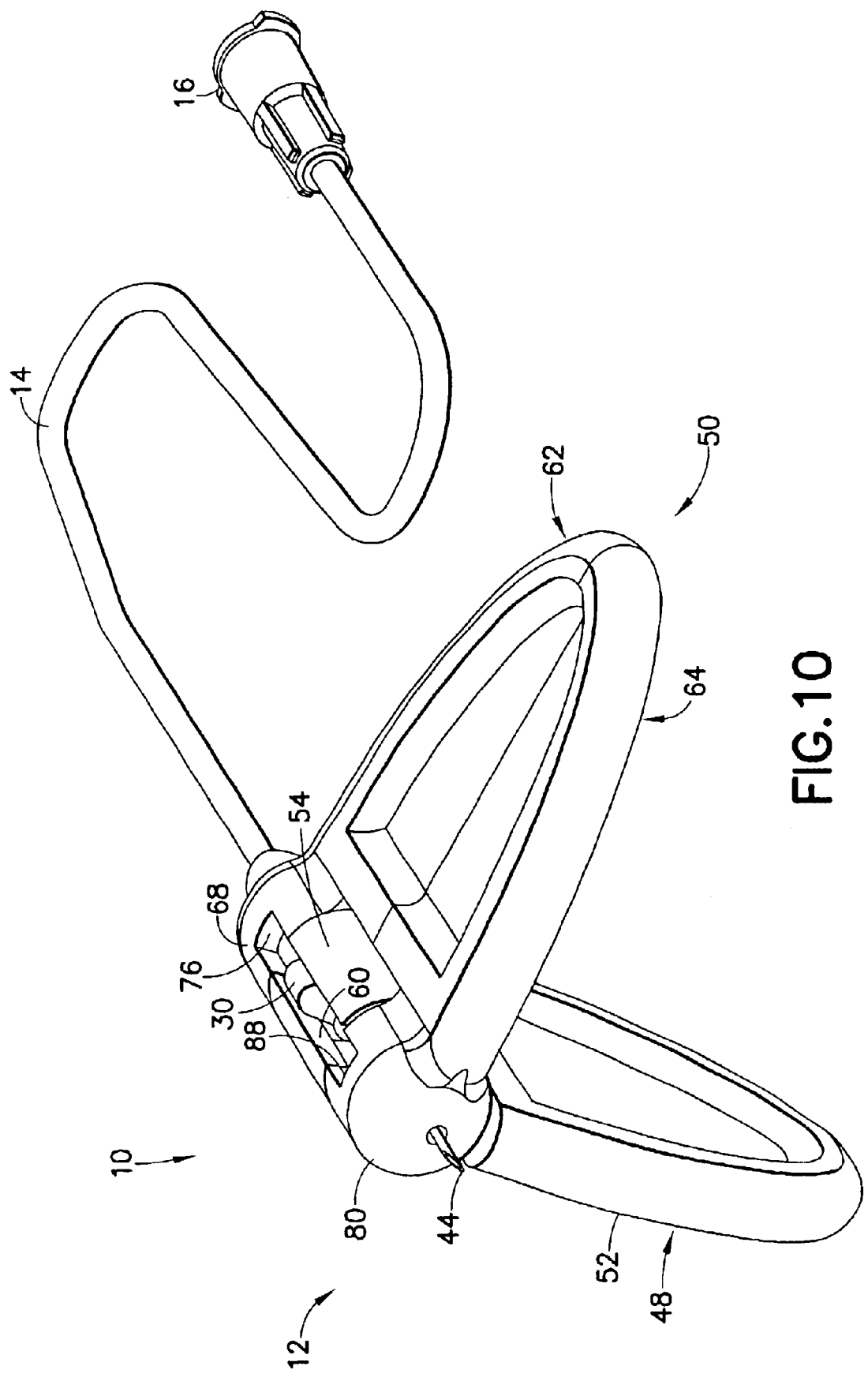
FIG. 10 is a perspective view similar to FIG. 8, but showing the needle cannula in a partly shielded condition.
Figure 11:
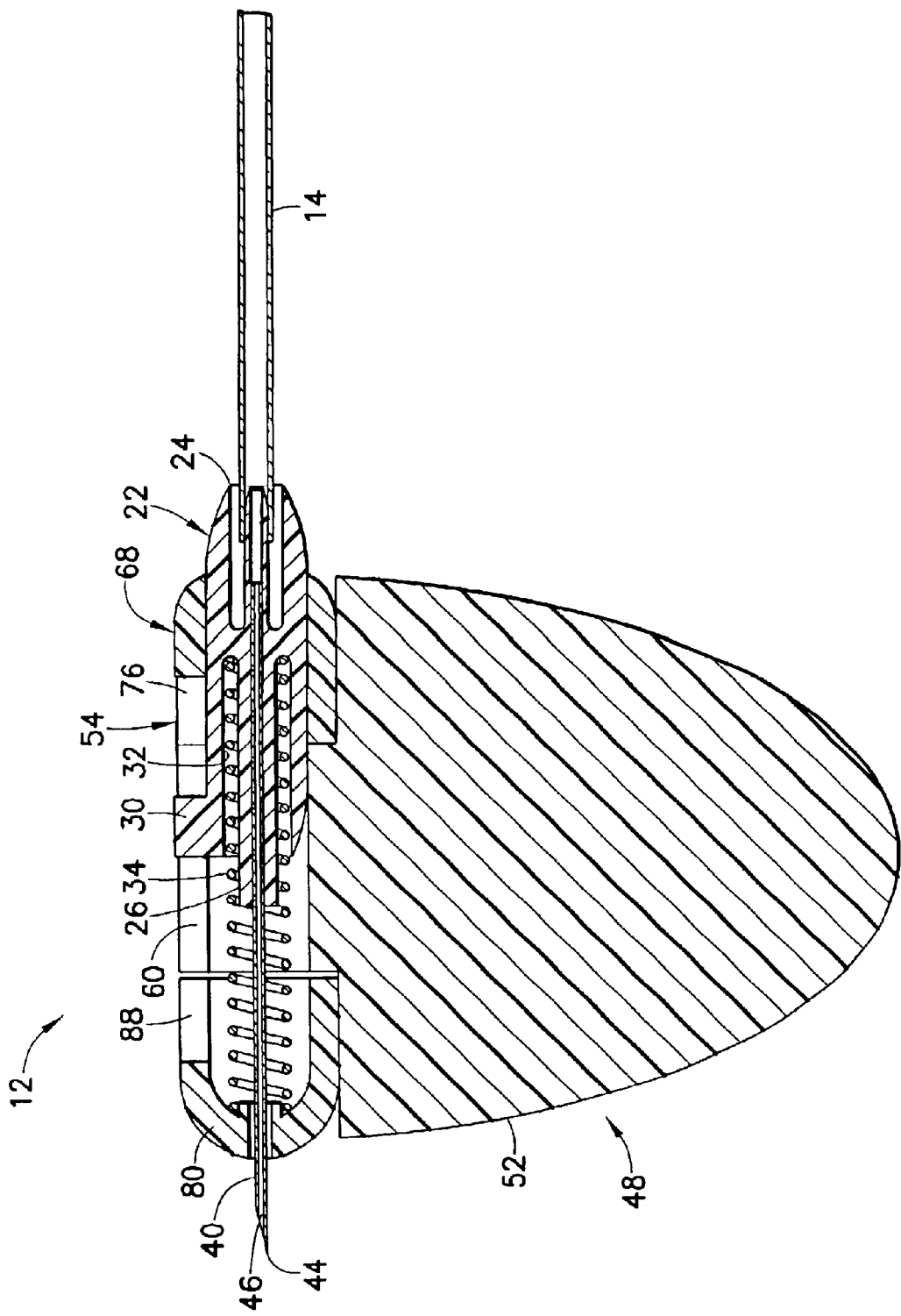
FIG. 11 is a cross-sectional view taken along line 11—11 of FIG. 10.
Figure 12:
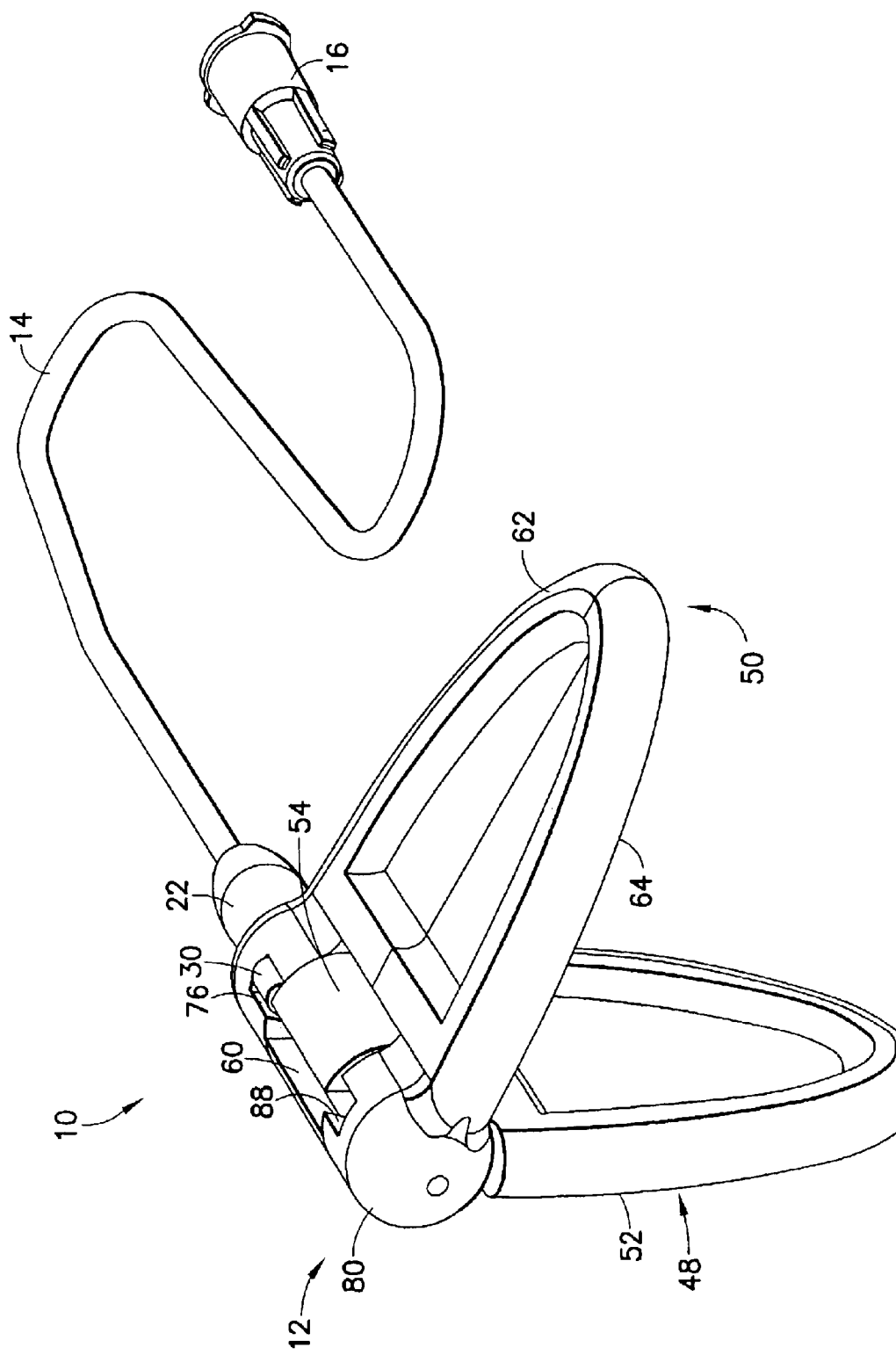
FIG. 12 is a perspective view similar to FIG. 10, but showing the needle cannula in the fully shielded position.
Figure 13:
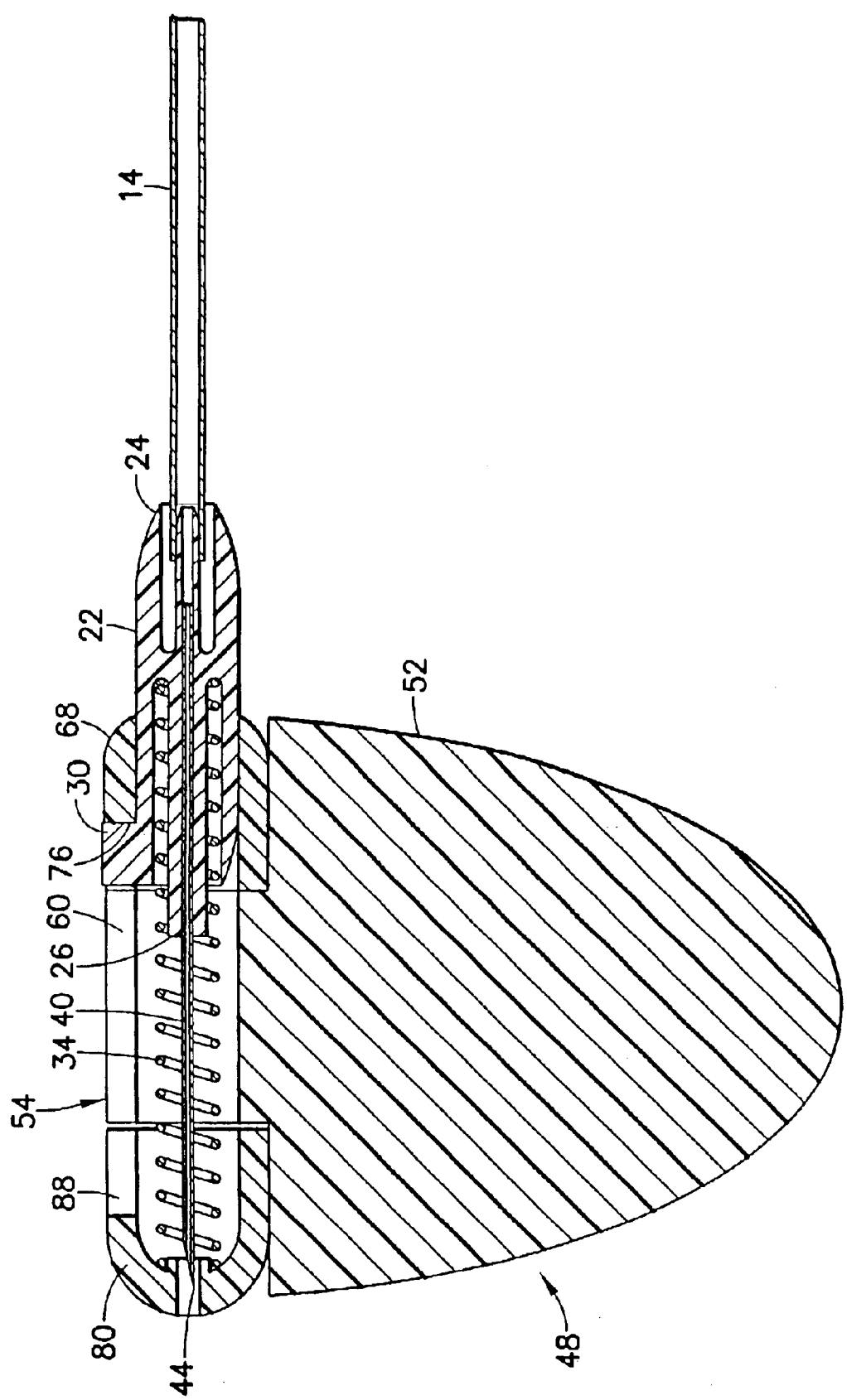
FIG. 13 is a cross-sectional view taken along line 13—13 in FIG. 12.

An IV infusion set or blood collection set in accordance with the subject invention is identified generally by the numeral 10 in FIGS. 1, 10 and 12, and for simplicity will be referred to herein as an IV infusion set. IV infusion set 10 includes a needle assembly 12, a length of flexible plastic tubing 14 and a fitting 16. Flexible tubing 14 includes a proximal end 18 and a distal end 20. Proximal end 18 of flexible plastic tubing 14 is secured to fitting 16. As illustrated herein, fitting 16 is a female luer fitting that communicates with the passage through tubing 14. However, other fittings may be employed, such as a non-patient needle assembly or a luer-activated device port.

Figure 6:
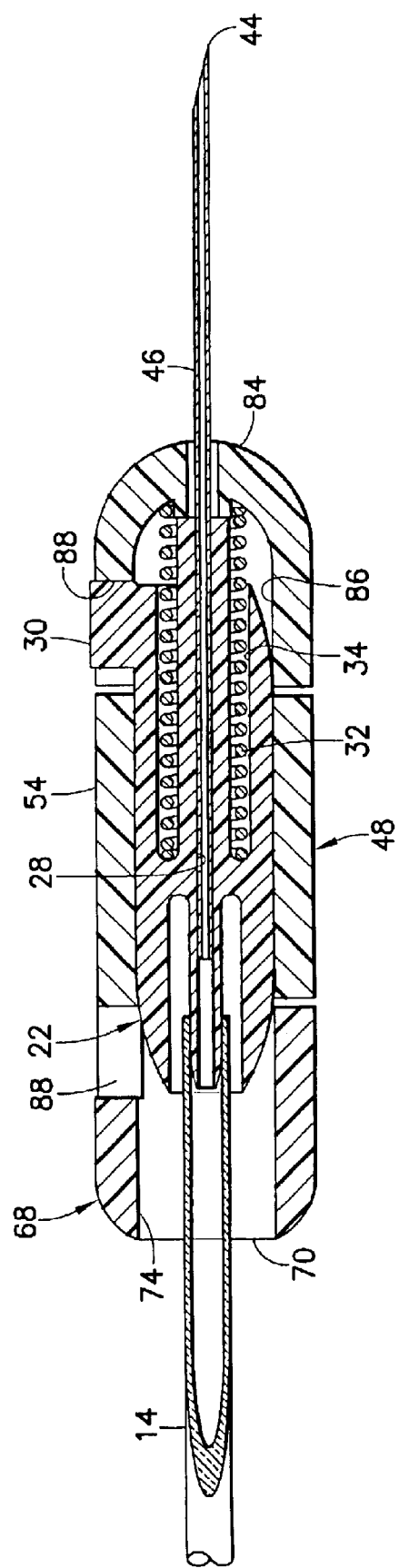
FIG. 6 is a cross-sectional view taken along line 6—6 in FIG. 5.
Figure 7:
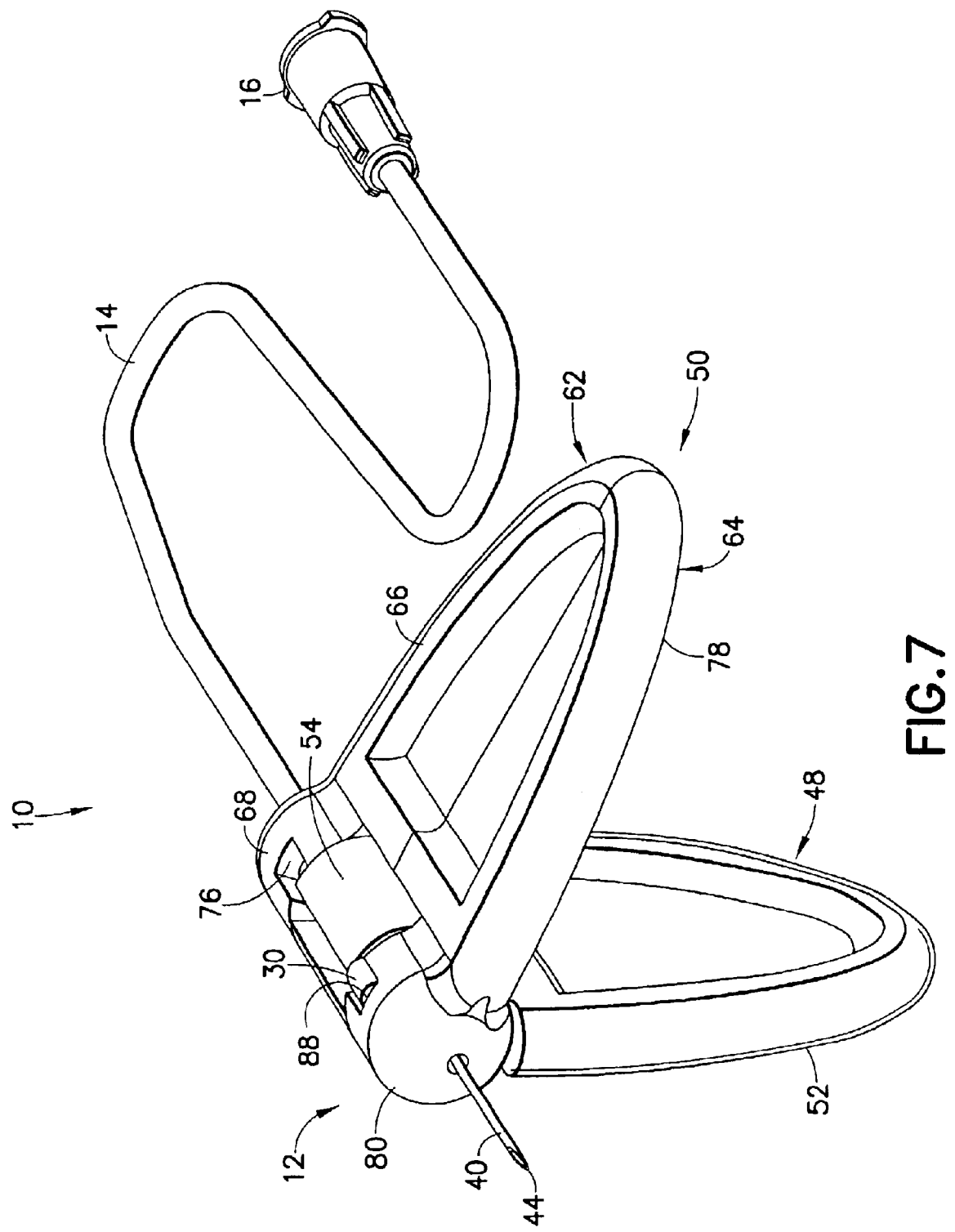
FIG. 7 is a perspective view showing movement of the wings toward one another after use of the IV infusion set.
Figure 8:
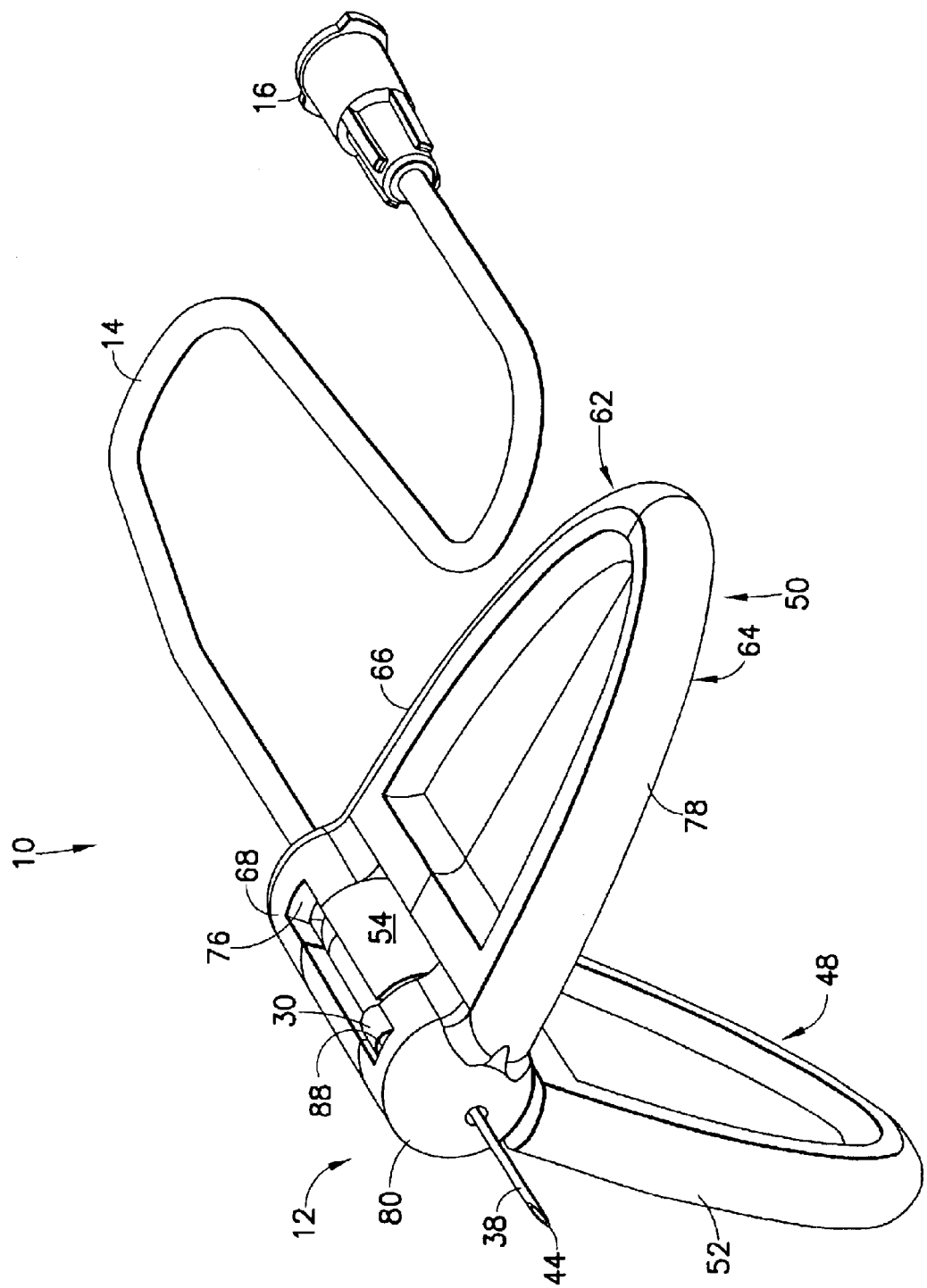
FIG. 8 is a perspective view similar to FIG. 7, but showing the wings rotated into a position to generate shielding of the needle cannula.
Figure 9:
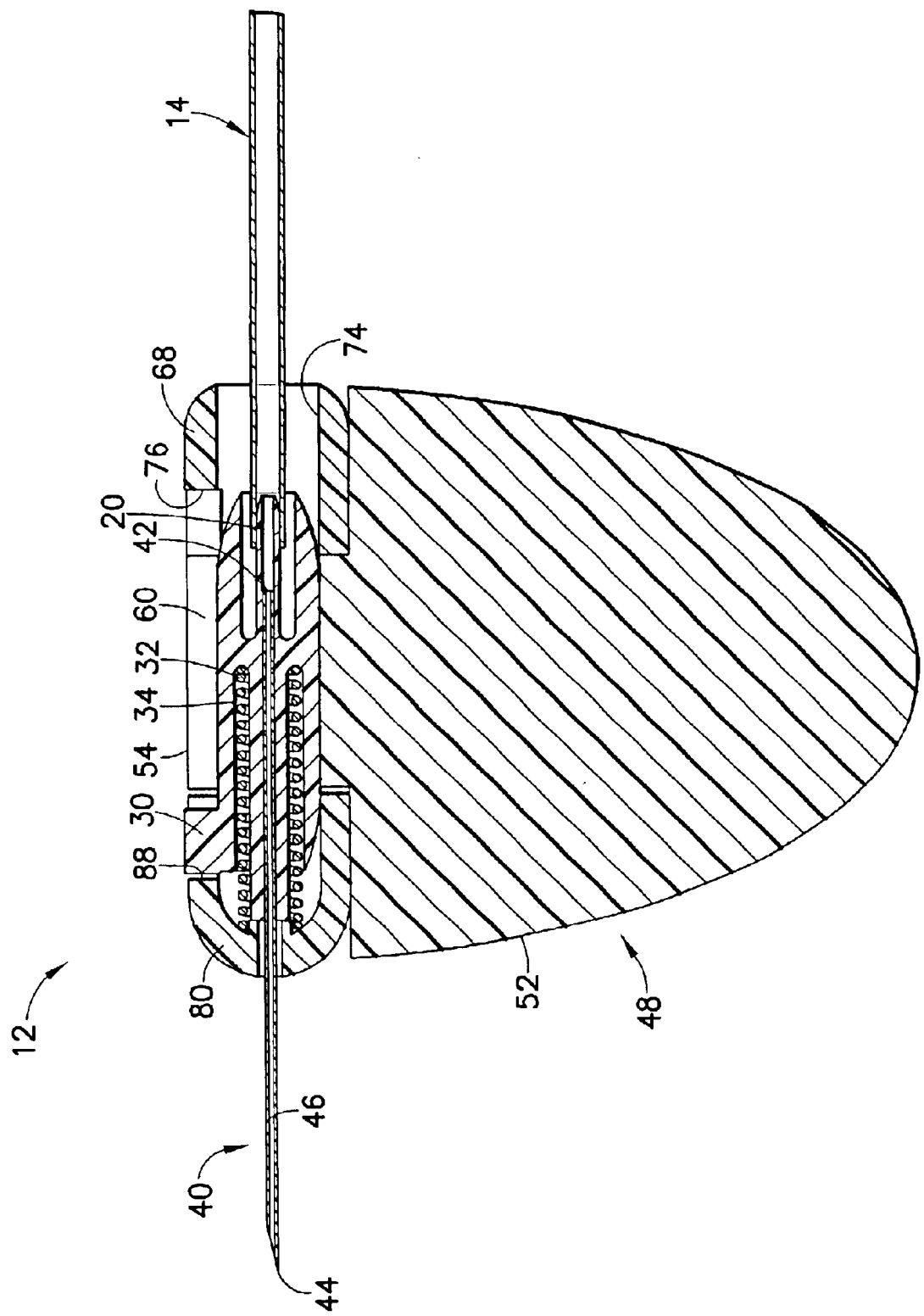
FIG. 9 is a cross-sectional view taken along line 9—9 of FIG. 8.

Needle assembly 12 includes a hub 22 that is formed unitarily from a transparent plastic material, such as polypropylene. Hub 22 includes a proximal end 24, a distal end 26 and a passage 28 extending between the ends. Distal end 20 of tubing 14 is mounted securely to proximal end 24 of hub 22 so that passage 28 through hub 22 communicates with the passage through tubing 14 and with fitting 16. A projection 30 projects unitarily out from outer circumferential surface of hub 22 substantially adjacent distal end 26 thereof. Projection 30 defines a circumferential dimension or width "a" and a length "b" as shown in FIG. 1. Distal end 26 of hub 22 is characterized further by a generally cylindrical spring recess 32 that is spaced outwardly from passage 28 and inwardly from projection 30, as shown in FIG. 6.

Needle assembly 12 also includes a coil spring 34 with a proximal end 36 and a distal end 38. Proximal end 36 of spring 34 is telescoped into spring recess 32 of hub 22. Spring 34 is dimensioned so that distal end 38 of spring 34 projects distally beyond hub 22 in an unbiased condition of spring 34 when proximal end 36 of spring 34 is mounted against the proximal end of spring recess 32.

Needle assembly 12 further includes a cannula 40 having a proximal end 42, a pointed distal end 44 and a lumen 46 extending between the ends. Proximal end 42 of cannula 40 is mounted securely in passage 28 of hub 22 so that pointed distal end 44 of cannula 40 projects distally beyond hub 22. As a result, lumen 46 of cannula 40 communicates with passage 28 of hub 22, with the passage through tubing 14 and with fitting 16.

Figure 4:
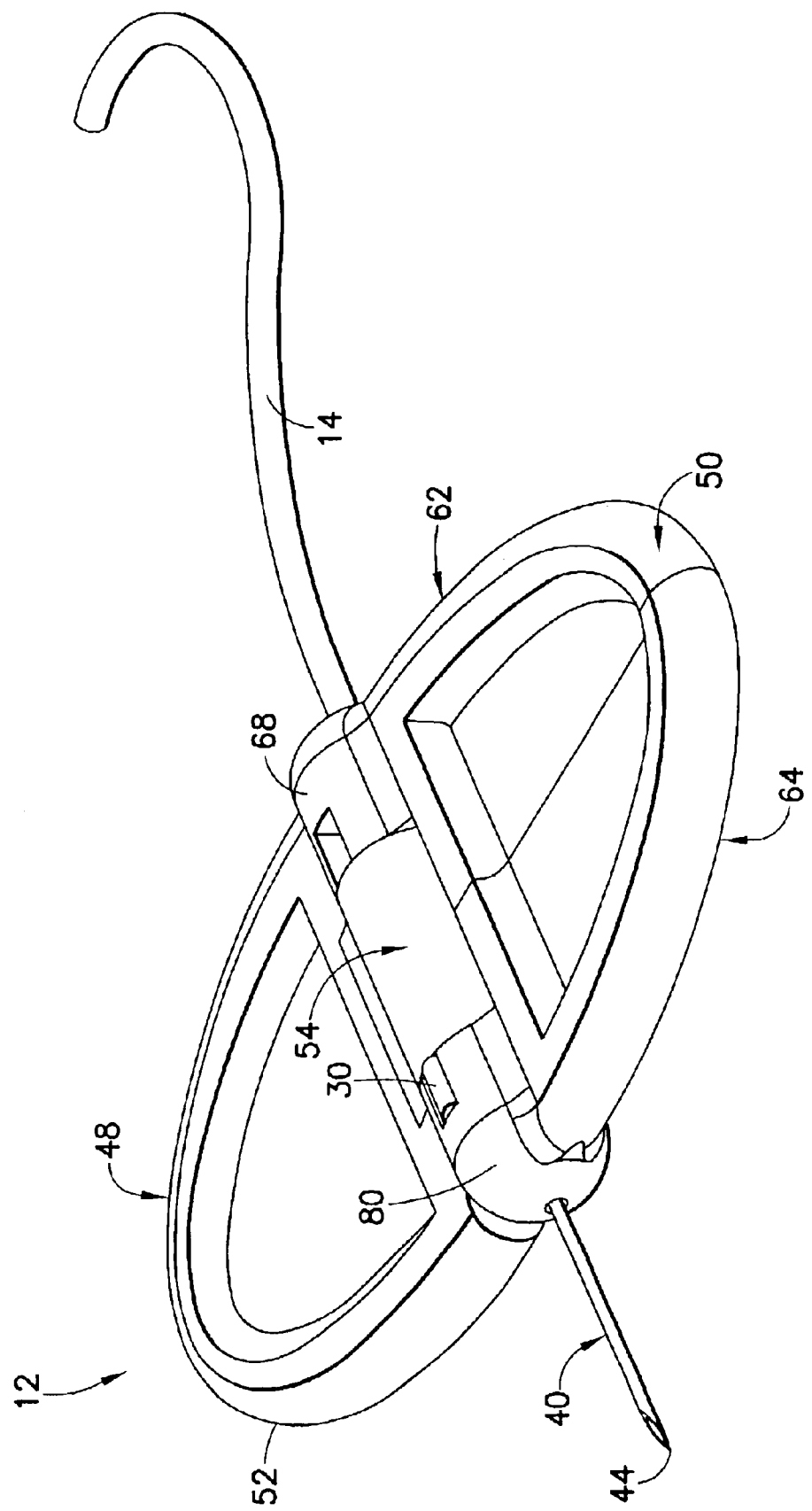
FIG. 4 is a perspective view of the needle assembly and tubing in an assembled condition and with the needle cannula projecting in a ready-to-use position.
Figure 5:
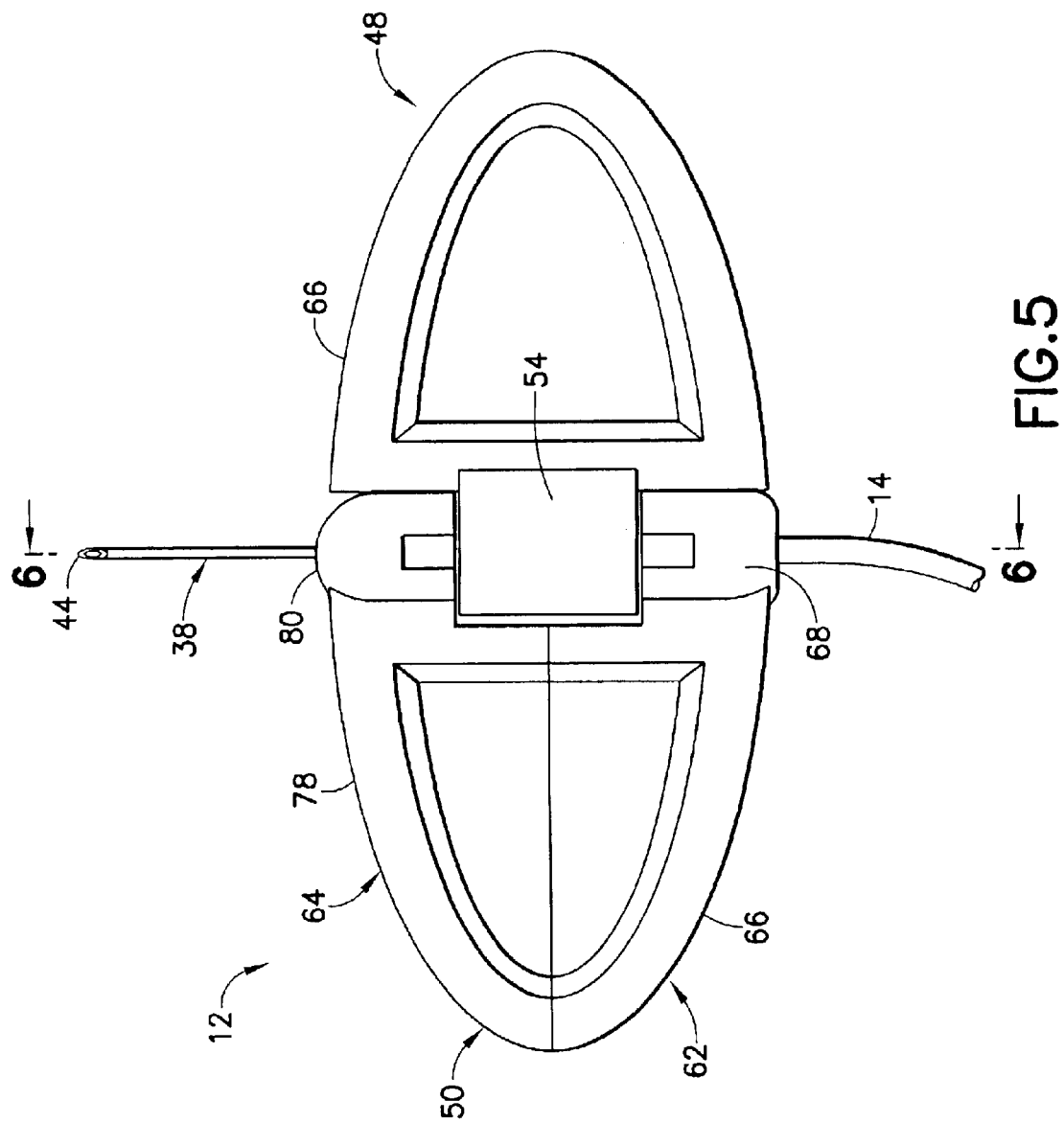
FIG. 5 is a top plan view of the needle assembly shown in FIG. 4.

Needle assembly 12 further includes first and second wings 48 and 50, as shown most clearly in FIG. 4. First wing 48 includes a panel 52 and a generally cylindrical center sleeve 54. Center sleeve 54 includes a proximal end 56, a distal end 58 and a slot 60 extending continuously between ends 56 and 58. Slot 60 is symmetrical with a diametric plane of center sleeve 54 that is coplanar with or parallel with panel 52. Slot 60 defines a width "c" that exceeds the width "a" of projection 30. Additionally, center sleeve 54 has an axial passage 61 with an inside diameter that exceeds the outside diameter of hub 22. Thus, center sleeve 54 can be telescoped axially over hub 22 by aligning slot 60 of center sleeve 54 with projection 30. Wing 48 can be rotated relative to hub 22 when center sleeve 54 is displaced axially from projection 30.

Center sleeve 54 preferably is substantially rigid to ensure secure mounting over hub 22 and efficient rotational and axial movement relative to hub 22. However, other portions of first wing 48 need not be rigid, and particularly center portions of panel 52 and lower surface regions of panel 52 conveniently are formed from a less rigid material. Thus, first wing 48 preferably is formed by a co-molding process where at least center sleeve 54 is formed from a rigid relatively stiff material and at least portions of panel 52 are formed from an elastomeric material. This co-molding may be achieved by initially forming center sleeve 54 and then over-molding at least portions of panel 52 over a connecting portion of center sleeve 54. Center sleeve 54 may be formed from polypropylene, whereas at least portions of panel 52 are formed from a thermoplastic elastomer, such as polyolefin, santoprene or soft PVC. Additionally, center sleeve 54 preferably is formed from a transparent plastic material to provide a clear indication of flashback as explained further herein.

Second wing 50 is formed from a proximal wing component 62 and a distal wing component 64 that are fused, sonically welded or adhered to one another. Proximal wing component 62 includes a proximal panel 66 and a proximal sleeve 68. Proximal sleeve 68 is formed from a rigid plastic material, such as polypropylene. Proximal panel 66 preferably is co-molded with proximal sleeve 68 and preferably is formed from a thermoplastic elastomer, as explained with respect to first wing 48. Proximal sleeve 68 is generally tubular and includes a proximal end 70, a distal end 72 and a cylindrical passage 74 extending between the ends. Passage 74 defines an inside diameter substantially equal to the inside diameter of passage 61 through center sleeve 54. Proximal sleeve 68 is characterized by a slot 76 that extends from distal end 72 of proximal sleeve 68 to a location between proximal and distal ends 70 and 72 of proximal sleeve 68. Slot 76 is symmetrical with a diametric plane of proximal sleeve 68 that is aligned substantially orthogonal to proximal panel 66. Slot 76 of proximal sleeve 68 has a circumferential dimension or width slightly greater than width "a" of projection 30 of hub 22 and a length slightly greater than length "b" of projection 30.

Distal wing component 64 includes a distal panel 78 and a distal sleeve 80. The distal wing component 64 is formed similar to proximal wing component 62, with distal sleeve 80 being formed from a substantially rigid material and at least portions of distal panel 78 being formed from a thermoplastic elastomer. Distal sleeve 80 includes a proximal end 82, a distal end 84 and a passage 86 extending between the ends. Portions of passage 86 adjacent proximal end 82 define an inside diameter slightly greater than the outside diameter of hub 22. However, portions of passage 86 adjacent distal end 84 define a diameter much smaller than the outside diameter of hub 22 and slightly greater than the diameter of cannula 40. Distal sleeve 80 is characterized by a slot 88 extending from proximal end 82 partway toward distal end 84. Slot 82 is symmetrical about a plane aligned orthogonal to distal panel 64. Additionally, slot 82 defines a width slightly greater than the width "a" of projection 30 on hub 22 and a length slightly greater than length "b" of projection 30.

IV infusion set 10 may be assembled by adhering or fusing distal end 20 of tubing 14 to proximal end 24 of hub 22. Additionally, proximal end 42 of cannula 40 is adhered, fused or otherwise secured in passage 28 through hub 22. The affixation of cannula 40 to hub 22 is carried out so that the bevel at distal end 44 of cannula 40 and projection 30 of hub 22 are symmetrical about a common plane and face the same radial direction. Assembly proceeds by telescoping spring 34 over cannula 40 and inserting proximal end 36 of spring 34 into spring recess 32 of hub 22. Thus, distal end 38 of unbiased spring 34 projects distally beyond spring recess 32.

Center sleeve 54 of first wing 48 then is telescoped in a proximal-to-distal direction over tubing 14 and over proximal end 24 of hub 22. This mounting is carried out with slot 62 rotationally offset from projection 30. Hence, the proximal-to-distal movement of center sleeve 54 will terminate when distal end 56 of center sleeve 54 abuts projection 30. Proximal wing component 62 then is telescoped over tubing 14 and over proximal end 24 of hub 20. The proximal-to-distal movement of proximal wing component 14 terminates when distal end 72 of proximal sleeve 68 abuts proximal end 58 of center sleeve 54.

Assembly proceeds by telescoping distal wing component 64 in a distal-to-proximal direction over cannula 40 and onto distal end 26 of hub 22. Distal wing component 64 is rotationally aligned so that projection 30 of hub 22 nests into slot 88 of distal sleeve 80. Proximal wing component 62 then is rotated relative to distal wing component 64 so that proximal panel 66 is coplanar with distal panel 78. Proximal and distal panels 66 and 78 are provided with mating pins and apertures to facilitate their alignment and positioning. In their aligned position, slot 82 of distal sleeve 80 aligns with slot 76 of proximal sleeve 68. Proximal and distal wing panels 66 and 78 then are fused together in a substantially coplanar disposition with slots 76 and 88 permanently aligned with one another. In this connected condition, spring 34 is compressed axially and hence maintains stored energy. Fitting 16 then is secured to proximal end 18 of tubing 14. Assembly may be completed by mounting a packaging cover (not shown) over cannula 40 and maintaining the packaging cover releasably in position by frictional engagement with distal sleeve 80 or by appropriate use of a tamper evident tape.

Panel 52 of first wing 48 initially is disposed in substantially coplanar relationship to panels 66, 78 of second wing 50. In this position, slot 60 of center sleeve 54 is approximately 90° offset from projection 30 on hub 22 and from slots 76 and 88 on proximal and distal sleeves 68 and 80 of second wing 50. Hence, projection 30 effectively is trapped between distal end 56 of center sleeve 54 and the distal end of distal sleeve 80. Accordingly, distal end 44 of cannula 40 projects distally beyond distal sleeve 80.

IV infusion set 10 may be used by connecting fitting 16 to an appropriate container that has a fluid that will be infused into a patient or a container for receiving a fluid specimen to be drawn from the patient. Panel 52 of first wing 48 and panel 66, 78 of second wing 50 then are rotated upwardly toward one another and into substantially face-to-face relationship. This upward rotation of first and second wings 48 and 50 causes slot 60 of center sleeve 54 to rotate into a position displaced approximately 180° from projection 30 of hub 22. Hence, projection 30 remains trapped in slot 88 of distal sleeve 80. The medical practitioner then removes the packaging cover from cannula 40 and guides pointed distal end 44 of cannula 40 into a targeted blood vessel. The disposition of needle cannula 40 ensures that the bevel at distal end 44 faces up for convenient guiding into the targeted blood vessel. Access to the blood vessel can be confirmed by the flashback evident in passage 28 as seen through the transparent plastic of hub 22 and of center sleeve 54. The medical practitioner then may rotate wings 48 and 50 away from one another so that panels 52, 66 and 78 lie in substantially face-to-face engagement with the skin of the patient. The panels may be taped in this mounted position.

Upon completion of the medical procedure, the user withdraws cannula 40 from the patient and urges panel 52 of first wing 48 and panel 66, 78 of second wing 50 downwardly and toward one another. As the wing panels 52 and 66, 78 approach perpendicular alignment with one another, slot 60 of center sleeve 54 moves into alignment with projection 30 of hub 22. As a result, stored energy in spring 34 will urge hub 22 proximally relative to wings 48 and 50 and through slot 60 of center sleeve 54. Thus, distal end 44 of cannula 40 will retract into distal sleeve 80 of second wing 50. Once projection 30 enters slot 76 of proximal sleeve 68, slot 60 will permit further downward rotation of wings 48 and 50 toward one another. Thus, slot 60 will be displaced rotationally from projection 30, and center sleeve 54 will hold projection 30 in slot 76 of proximal sleeve. IV infusion assembly 10 then may be discarded in a sharps receptacle with cannula 40 safely retracted.

Although not shown, slot 76 in proximal sleeve 68 may be formed with one or more locking detents. The locking detents may include a distal inclined face and a proximal locking face. Spring 34 will guide projection 30 over the inclined distal face of the locking detent. However, projection 30 then will be trapped behind the proximal locking face of the locking detent. Alternatively, spring fingers or detents may be formed on wings 48 and 50. The spring fingers or detents may be disposed and configured to prevent wings 48 and 50 from returning to a position where cannula 40 can be re-exposed.

As an alternative to the embodiment described and illustrated above, slot 60 of center sleeve 54 may be disposed to align with projection 30 when first panel 52 is substantially coplanar with second panel 66, 78. With this embodiment, spring 34 must be selected to exert forces that are less than frictional forces between cannula 40 and the tissue of the patient. This embodiment is employed substantially as described above by initially holding wings 48 and 50 in face-to-face engagement with one another for insertion of cannula 40 into the patient. Wings 48 and 50 then will be rotated away from one another and into a substantially coplanar disposition adjacent the skin of the patient. This alignment of wings 48 and 50 will dispose slot 60 in a rotational position aligned with projection 30. However, the frictional forces on cannula 40 will hold cannula 40 and hub 22 in at least a partly extended position. The frictional forces on cannula 40 will gradually reduce as cannula 40 is being withdrawn from the patient. As a result, spring 34 will exert sufficient forces to propel hub 22 and cannula 40 proximally and into a position where cannula 40 is safely shielded.

The preceding embodiment relates to automatic shielding initiated merely by an appropriate rotational alignment of wings 48 and 50 and the driving force of spring 34. However, a manually shieldable spring-assisted version of the invention can be provided merely by removing spring 34 and/or extending projection 30 sufficiently to project through the slots of the sleeves of the wings. Thus, shielding can be effected by rotating the wings into a position where the slots align with one another and then manually moving the projection in a proximal direction to effect shielding.

The preceding embodiments show the slots 60, 76 and 88 defining widths that are substantially equal to one another and slightly greater than the width "a" of projection 30. However, the slots 60, 76 and 88 need not be of equal widths. For example, slot 76 of proximal sleeve 68 may be wider than slot 88 of distal sleeve 80 to facilitate entry of projection 30 into slot 76. Additionally, slot 60 of center sleeve 54 may be significantly wider than slot 88 of distal sleeve to increase the range of angular positions at which shielding will commence. Thus, shielding will commence at any of a range of angular orientations, and not merely at a single rotational orientation of wings 48 and 50. These and other variations will be apparent to a person skilled in this art after having read the subject disclosure.

What is claimed is:

1. A needle assembly comprising:
   a hub having opposite proximal and distal ends and a passage extending between said ends, a projection extending outwardly from said hub;
   a cannula having a proximal end mounted in said passage of said hub and a distal end projecting distally from said hub;
   a first wing having a center sleeve rotatably and axially movable on said hub, said center sleeve having opposite proximal and distal ends and a slot extending between said ends, said slot being dimensioned to slidably accommodate said projection on said hub; and
   a second wing having proximal and distal sleeves disposed respectively substantially adjacent said proximal and distal ends of said center sleeve of said first wing, said proximal and distal sleeves being rotatably and axially movable on said hub, at least said distal sleeve including a slot formed therein and slidably receiving said projection of said hub, said first and second wings being rotatable relative to one another from a first position where said slots of said first and second wings are misaligned and a second position where said slots of said first and second wings are aligned for permitting axial movement of said projection of said hub from a first position where said cannula is exposed from said sleeves to a second position where said cannula is substantially shielded within said sleeves.

2. The needle assembly of claim 1, wherein said proximal sleeve includes a slot dimensioned for receiving said projection.

3. The needle assembly of claim 2, wherein said wings are rotatable to a third position where said slots of said wings are misaligned for locking said hub in said slot of said proximal sleeve.

4. The needle assembly of claim 2, wherein said slot of said proximal sleeve is aligned with said slot of said distal sleeve.

5. The needle assembly of claim 4, wherein said slot of said center sleeve is substantially symmetrical with a diametric plane of said center sleeve substantially parallel to said panel of the first wing.

6. The needle assembly of claim 1, wherein said first wing includes a panel extending from said center sleeve and said second wing includes a panel extending from said proximal and distal sleeves, said slot in said distal sleeve being symmetrical with a diametric plane of said distal sleeve substantially orthogonal to said second panel.

7. The needle assembly of claim 1, wherein said slot of said center sleeve extends entirely through said center sleeve in a radial direction.

8. The needle assembly of claim 1, wherein said slot of said distal sleeve extends entirely through said distal sleeve from an inner circumferential surface thereof to an outer circumferential surface thereof.

9. The needle assembly of claim 8, wherein said projection extends radially through said slot to a location radially beyond the outer circumferential surface of said proximal sleeve.

10. The needle assembly of claim 1, wherein at least portions of said hub include a substantially cylindrical outer surface.

11. The needle assembly of claim 1, wherein said center sleeve includes a substantially cylindrical inner circumferential surface.

12. The needle assembly of claim 1, further comprising a spring between said hub and said second wing for biasing said hub into a retracted position relative to said sleeves.

13. The needle assembly of claim 1, wherein each said sleeve is formed from a rigid material and wherein at least portions of each said panel are formed from a flexible material.

14. The needle assembly of claim 13, further comprising a fitting secured to an end of said flexible tubing remote from said hub.

15. The needle assembly of claim 1, further comprising a length of flexible tubing connected to said proximal end of said hub.

16. The needle assembly of claim 1, wherein said hub and at least said center sleeve are formed from a transparent material for facilitating indication of venous access.

17. The needle assembly of claim 1, wherein said second wing is formed from proximal and distal wing components, said proximal wing component including said proximal sleeve and said distal wing component including said distal sleeve.

18. A needle assembly comprising:

a hub having opposite proximal and distal ends and a passage extending between said ends, a projection extending outwardly from said hub;

a cannula having a proximal end mounted in said passage of said hub and a distal end projecting distally from said hub;

a first wing having a center sleeve rotatably and axially movable on said hub, said center sleeve having opposite proximal and distal ends and a slot extending between said ends, said slot being dimensioned to slidably accommodate said projection on said hub; and a second wing having proximal and distal sleeves disposed respectively substantially adjacent said proximal and distal ends of said center sleeve of said first wing, said proximal and distal sleeves being rotatably and axially movable on said hub, said proximal and distal sleeves each including a slot formed therein, said slots being aligned with one another and being dimensioned for receiving said projection of said hub, said first and second wings being rotatable relative to one another from a first position where said slots of said first and second wings are misaligned and a second position where said slots of said first and second wings are aligned for permitting axial movement of said projection of said hub from said slot in said distal sleeve, through said slot in said center sleeve and into said slot of said proximal sleeve, said cannula being disposed entirely within said sleeves when said projection is in said slot of said proximal sleeve; and a spring for biasing said hub proximally relative to said sleeves.

19. A method for using and shielding a needle assembly, said needle assembly having a hub and a cannula projecting therefrom and a pair of wings rotatably and axially movable relative to said hub, said method comprising the steps of:

rotatably moving said wings in a first rotatable direction from a first rotatable position where said wings are substantially coplanar to a second rotatable position where said wings are substantially adjacent;

gripping said wings in said second rotational position for accessing an injection site with said cannula;

rotating said wing in a second rotational direction opposite to said first rotational direction and back to said first rotational position where said wings are substantially coplanar;

removing said cannula from said injection site and rotating said wings further in said second rotational direction and into a third rotational position;

moving said hub and said cannula proximally relative to said wings and into a retracted position where said cannula is shielded; and rotating said wings further in said second rotational direction and into a fourth rotational position where said wings cooperate to hold said hub and said cannula in said retracted position.

* * * * *